United States Patent
Koch et al.

(10) Patent No.: US 7,942,389 B2
(45) Date of Patent: May 17, 2011

(54) AIR HUMIDIFIER FOR RESPIRATORS AND INCUBATORS

(75) Inventors: Jochim Koch, Ratzeburg (DE); Klaus Radomski, Lübeck (DE); Andreas Krause, Lübeck (DE)

(73) Assignee: Dräger Medical GmbH, Lübeck (DE)

( * ) Notice: Subject to any disclaimer, the term of this patent is extended or adjusted under 35 U.S.C. 154(b) by 972 days.

(21) Appl. No.: 11/778,758

(22) Filed: Jul. 17, 2007

(65) Prior Publication Data

US 2008/0042304 A1 Feb. 21, 2008

(30) Foreign Application Priority Data

Aug. 17, 2006 (DE) .................. 10 2006 038 754

(51) Int. Cl.
*B01F 3/04* (2006.01)
(52) U.S. Cl. ....... 261/130; 261/72.1; 261/133; 261/142; 128/203.27
(58) Field of Classification Search ........... 261/72.1, 261/130, 133, 141, 142, DIG. 65; 128/203.17, 128/203.27
See application file for complete search history.

(56) References Cited

U.S. PATENT DOCUMENTS

| | | | | |
|---|---|---|---|---|
| 2,302,528 A * | 11/1942 | Conklin | ............ | 236/44 A |
| 4,051,205 A * | 9/1977 | Grant | ............ | 261/70 |
| 4,110,419 A * | 8/1978 | Miller | ............ | 261/142 |
| 4,346,048 A * | 8/1982 | Gates | ............ | 261/130 |
| 4,366,105 A * | 12/1982 | Nowacki | ............ | 261/35 |
| 4,430,994 A * | 2/1984 | Clawson et al. | ............ | 128/203.27 |
| 4,500,480 A * | 2/1985 | Cambio, Jr. | ............ | 261/104 |
| 4,674,494 A * | 6/1987 | Wiencek | ............ | 128/203.16 |
| 4,765,327 A * | 8/1988 | Shim | ............ | 128/204.13 |
| 6,031,968 A * | 2/2000 | Holtmann | ............ | 392/402 |
| 6,169,852 B1 * | 1/2001 | Liao et al. | ............ | 392/395 |
| 6,988,497 B2 * | 1/2006 | Levine | ............ | 128/203.27 |
| 6,997,183 B2 | 2/2006 | Koch et al. | | |
| 7,228,859 B2 * | 6/2007 | Loescher | ............ | 128/203.12 |
| 7,694,675 B2 * | 4/2010 | Koch et al. | ............ | 128/203.17 |
| 2004/0221843 A1 * | 11/2004 | Baecke | ............ | 128/203.16 |
| 2004/0261951 A1 * | 12/2004 | Baecke | ............ | 159/47.1 |
| 2006/0144395 A1 | 7/2006 | Koch et al. | | |

FOREIGN PATENT DOCUMENTS

DE 102 34 811 C1 11/2003
DE 102005000690 B3 5/2006

* cited by examiner

*Primary Examiner* — Scott Bushey
(74) *Attorney, Agent, or Firm* — McGlew and Tuttle, P.C.

(57) ABSTRACT

An evaporator defines an evaporator volume, and boils the liquid inside evaporator volume. A mixing chamber is in communication with the evaporator volume and mixes the vapor or moisture from the liquid in the evaporator with the breathing gas of the patient. The mixing chamber is a separate structure than the evaporator. The mixing chamber and the evaporator are connected by a first connection that is repetitively connectable and disconnectable without significant destruction of a respective connection. A heater is arranged outside of the evaporator and in a heat conducting connection with the evaporator. The heater is a separate structure than the evaporator. The evaporator and the heater are connected by a second connection that is repetitively connectable and disconnectable. A liquid storage tank is in communication with the evaporator and supplies a liquid to the evaporator through a flow channel. The liquid storage tank is larger than the evaporator. The flow channel is formed of a material and has a size to thermally insulate the evaporator from the liquid storage tank.

20 Claims, 2 Drawing Sheets

AIR HUMIDIFIER FOR RESPIRATORS AND INCUBATORS

CROSS REFERENCE TO RELATED APPLICATIONS

This application claims the benefit of priority under 35 U.S.C. §119 of German Patent Application 10 2006 038 754.6 filed Aug. 17, 2006, the entire contents of which are incorporated herein by reference.

FIELD OF THE INVENTION

The present invention pertains to an air humidifier for respirators and incubators.

BACKGROUND OF THE INVENTION

Various air humidifiers for respirators and/or incubators have been proposed, which are more or less complicated in terms of design or handling, or are associated with the risk that the water reserve used becomes contaminated with microbes due to their design.

A prior-art air humidifier or air moistener has a simple hot plate with a water reservoir in a pot-shaped container, through which the breathing gas is passed and thus humidified. This prior-art concept has, however, the drawback that the total amount of water must at first be heated up before the humidifier can deliver its full moistening capacity. This may take up to 30 minutes, so that a patient connected to the moistener may not be sufficiently humidified during this time. It is also disadvantageous in this arrangement that the water may become contaminated with microbes over time because the temperatures are not high enough.

A breathing moistener with an automatic water refilling means and an electrically heated evaporator has become known from DE 10 2005 000 690 B3, in which the evaporator has a tubular housing, which is filled with a porous material. One side of the housing is in liquid connection with the water refilling means, and the other side is in connection with an evaporator chamber through which breathing gas flows. This breathing moistener is characterized in that it is equipped with a certain, porous sintered glass or ceramic in a first, lower, unheated area, and is equipped with a certain, porous sintered metal in a second, upper, heated area.

Another breathing moistening system appears from DE 102 34 811 C1, in which the user must only refill the water reserve for one night into a container for a home respirator. The drawback of this arrangement is that not all the parts that come into contact with the water can be removed and cleaned in a simple manner.

SUMMARY OF THE INVENTION

The object of the present invention is to provide an air humidifier for respirators and incubators, which is operated at the boiling point of water, and which has a simple design and offers the possibility of removing and cleaning the parts that come into contact with the breathing gas and the water, for example, in a dishwasher.

The object is accomplished inside a device for adding moisture to breathing gas of a patient. An evaporator defines an evaporator volume, and boils the liquid inside the evaporator volume. A mixing chamber is in communication with the evaporator volume and mixes the vapor or moisture from the liquid in the evaporator with the breathing gas of the patient. The mixing chamber is a separate structure from the evaporator. The mixing chamber and the evaporator are connected by a first connection that is repetitively connectable and disconnectable without significant destruction of a respective connection. The phrase "without significant destruction" is used to indicate that the connections are designed to operate for the expected lifetime of the evaporator, heater and breathing gas supply without repair or major modification. A heater is arranged outside of the evaporator and in a heat conducting connection with the evaporator. The heater is a separate structure than the evaporator. The evaporator and the heater are connected by a second connection that is repetitively connectable and disconnectable. A liquid storage tank is in communication with the evaporator and supplies a liquid to the evaporator through a flow channel. The liquid storage tank is larger than the evaporator. The flow channel is formed of a material and has a size to thermally insulate the evaporator from the liquid storage tank.

The essential advantage of the air humidifier according to the principal claim is that the electric heater is separated from the water storage tank and from the evaporator, both of which can be removed and cleaned separately. There are no electric contacts or components on the water storage tank and on the evaporator proper. The water storage tank is thermally separated from the evaporator, so that only a small amount of water is being heated and evaporated. The air humidifier can as a consequence also be heated up rapidly and it rapidly responds to changes in the set heating output.

The water tank and the evaporator can be manufactured at low cost, so that these components may also be offered as disposable articles. The air humidifier may also be operated with tap water, because the minerals deposited from the water can again be removed during cleaning, optionally by mechanical cleaning by brushing, especially because all relevant openings of the air humidifier are large enough.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENT

Figure 1:
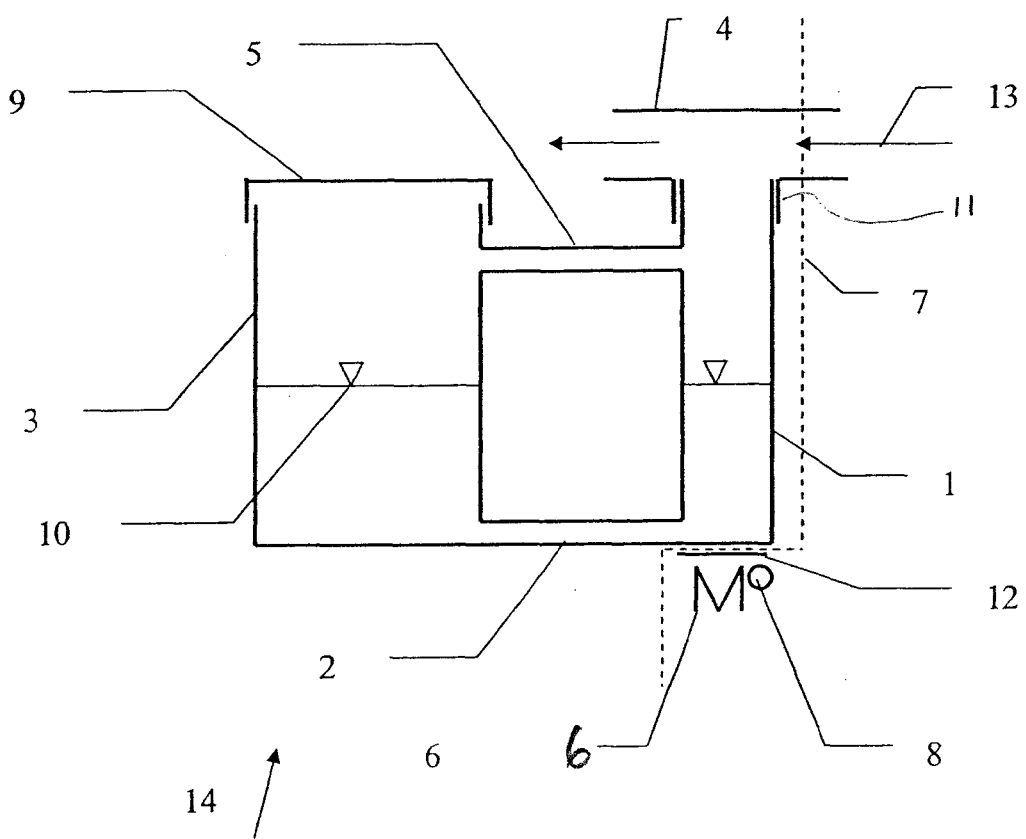
FIG. 1 is a schematic view of an air humidifier.

Referring to the drawings in particular, FIG. 1 shows an entire air humidifier 14 according to the invention. A liquid storage tank, preferably a water storage tank 3, is connected to an evaporator 1. The evaporator 1 is operated at the boiling point via a narrow flow channel 2 with a diameter of a few mm, which acts as a thermal insulation or sink The evaporator 1 is in thermal connection with the electric heater 6 of the device 7 (respirator or incubator) via the contact surface connection 12. The connection between the evaporator 1 and the heater 6 is preferably just a supporting connection where the weight of the evaporator 1 holds the evaporator 1 on the heater 6. The water level 10 is equal in the two tanks shown. The water storage tank 3 is closed airtightly against a respirator, not shown in more detail, with a cover 9. The heater 6 is controlled by a control circuit of the device 7 in terms of the temperature, measured by means of a temperature sensor 8, such as a PTC element, or controlled on the basis of the heating output. If a respiration pressure is present, i.e., in case of use at a respirator, pressure equalization with the water storage tank 3 is established via an optional pressure equalization line 5, so that the water level 10 remains constant in the evaporator 1. The water vapor mixes with the breathing gas 13 in the mixing chamber 4. The connection 11 between the evaporator 1 and the mixing chamber 4 is shown as a simple plug-in or slide in connection. In order to prevent leakage, this connection 11 should be very tight but still possess good sliding properties. In the alternative, a seal can be arranged between the evaporator 1 and the mixing chamber 4, or a clamping arrangement can be provided to connect the evaporator 1 with the mixing chamber 4.

When the air humidifier 14 is used, as an alternative, for or with an incubator, a separate mixing chamber 4 may be eliminated. The water vapor can be fed directly into the air circulation in an incubator which forms its own mixing chamber. The non-electric combination/portion of the air humidifier 14 can be removed from the device 7, i.e., a respirator or optionally also an incubator, without the electric components corresponding to the separation line drawn as a broken line in FIG. 1.

Figure 2:
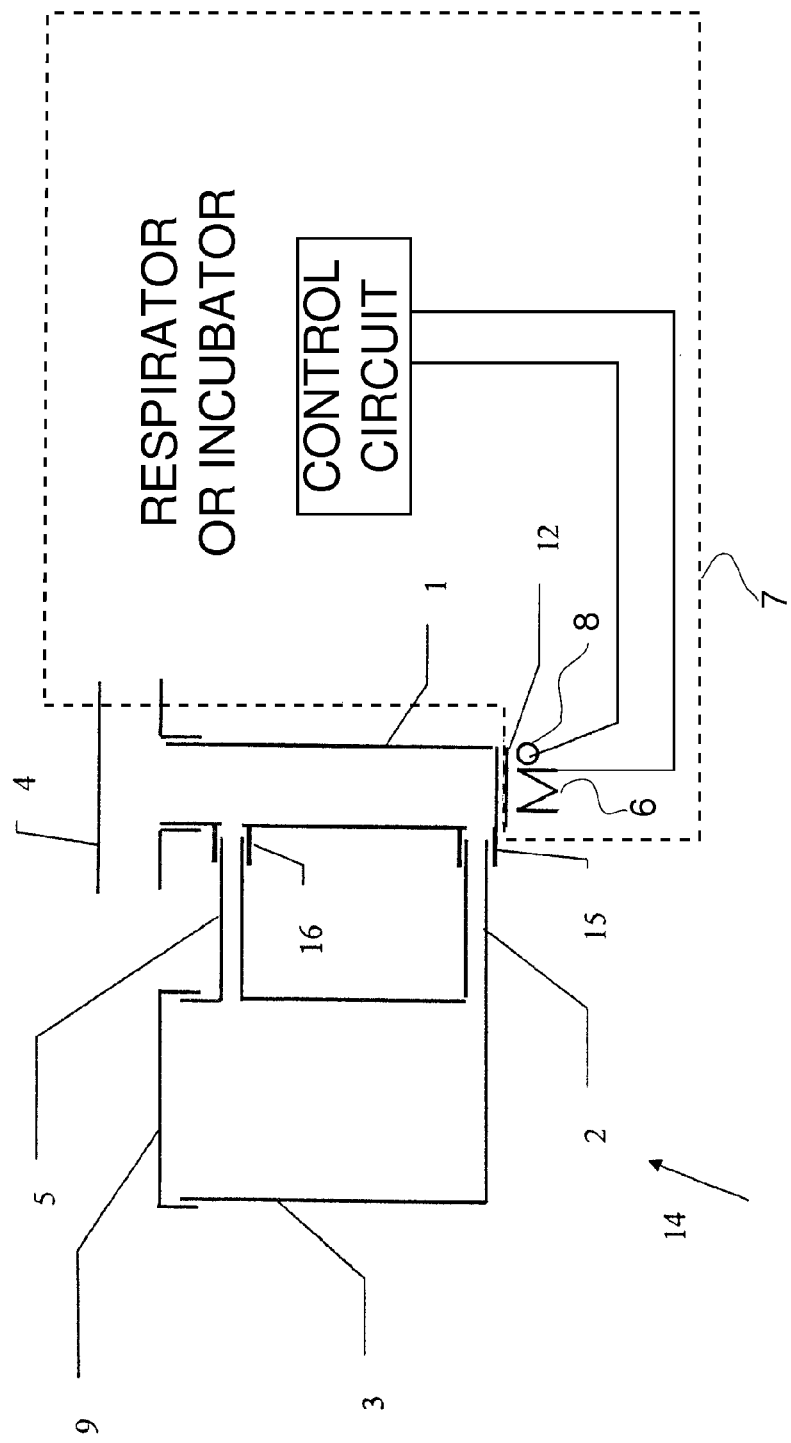
FIG. 2 is a schematic view showing design details of the arrangement according to FIG. 1.

FIG. 2 shows the detailed design. The water storage tank 3 is made, for example, of a plastic by injection molding. It is sealed with a closable cover 9 to ensure that the respiration pressure of the respirator cannot escape. The water storage tank 3 is connected to the evaporator 1 via plug-in connections 15, 16. The evaporator 1 may consist, for example, of a material with good thermal conductivity, for example, salt-water-resistant aluminum, and is manufactured especially by diecasting. The mixing chamber 4 establishes the connected between the respirator and the breathing tube to the patient. The mixing chamber 4 is manufactured especially from a plastic by injection molding.

The desired thermal insulation between the evaporator 1 and the water storage tank 3 via the flow channel 2 and, if present, via the pressure equalization line 5 is brought about by manufacturing the water storage tank 3 and the elements 2 and 5 from a plastic such as PSU, PC, PA with a coefficient of heat conduction of about 0.2 W/(m·K). If a tube external diameter of 10 mm and an internal diameter of 6 mm and a length of, e.g., 50 mm are selected, a C (coefficient of heat transmission) value of 4 W/(m$^2$·K) is obtained. There also is additionally a heat conduction via the water. To prevent the water from being able to circulate in the tube, the internal diameter of the flow channel 2 should be limited to 6 mm. The total value of heat conduction thus increases to a C value of about 4.6 W/(m$^2$·K). The consequence of this would be that the water storage tank 3 would heat up by about 5 C over a period of 8 hours (one night). It is thus guaranteed that the water in the water storage tank 3 will not be heated intensely and cannot boil by any means or cannot extract too much heating output from the heater 6.

The size of the water storage tank 3 and the evaporator 1 are dimensioned depending on the desired operating time for one water filling. It is important for good thermal efficiency for heating the water that the heated bottom surface of the evaporator 1 be substantially smaller than that of the water storage tank 3, especially ⅕ to 1/10 of the base of the water storage tank 3.

While specific embodiments of the invention have been shown and described in detail to illustrate the application of the principles of the invention, it will be understood that the invention may be embodied otherwise without departing from such principles.

What is claimed is:

1. An air humidifier for a respirator or incubator, the humidifier comprising:
    a liquid storage tank;
    an evaporator in liquid connection with said liquid storage tank and operating at a boiling point of a liquid in said liquid storage tank;
    a flow channel forming said liquid connection between said liquid storage tank and said evaporator, said flow channel acting as a heat insulator in a bottom area of said evaporator;
    a heater in a heat-conducting connection with said evaporator, said heater being part of the respirator or incubator designated as a breathing gas supply;
    a mixing chamber of the respirator or the incubator, said mixing chamber being in flow connection with said evaporator;
    said evaporator being detachably connected to the respirator or the incubator, said liquid storage tank and said evaporator being removable from the respirator or the incubator.

2. An air humidifier in accordance with claim 1, wherein:
    said liquid storage tank has a pressure equalization line to said evaporator and is in gas flow connection with said mixing chamber, said pressure equalization line being above a liquid level of said liquid storage tank.

3. An air humidifier in accordance with claim 1, wherein:
    said evaporator consists of an aluminum alloy.

4. An air humidifier in accordance with claim 1, further comprising:
    a control circuit, said heater being controlled by said control circuit with a temperature sensor.

5. An air humidifier in accordance with claim 1, further comprising:
    a PTC element, said heater being controlled by said PTC element.

6. An air humidifier in accordance with claim 1, wherein:
    said liquid storage tank is manufactured from a plastic by injection molding.

7. An air humidifier in accordance with claim 1, wherein:
    said water storage tank is detachably connected to said evaporator by means of at least one plug-in connection.

8. An air humidifier in accordance with claim 1, further comprising:
    a cover, said water storage tank being closed airtightly with said cover.

9. An air humidifier in accordance with claim 1, wherein:
    a heated base or bottom surface of said evaporator is smaller than a base or bottom surface of said liquid storage tank.

10. An air humidifier in accordance with claim 1, wherein:
    a heated base or bottom surface of said evaporator is smaller than a base or bottom surface of said liquid storage tank by a ratio ranging from 1:5 to 1:10.

11. An air humidifier in accordance with claim 2, wherein:
    said evaporator consists of an aluminum alloy;
    said heater is controlled by a control circuit with a temperature sensor;
    said heater is controlled by a PTC element;
    said liquid storage tank is manufactured from a plastic by injection molding;
    said water storage tank is detachably connected to said evaporator by means of at least one plug-in connection;
    said water storage tank is closed airtightly with a cover;
    a heated base or bottom surface of said evaporator is smaller than a base or bottom surface of said liquid storage tank by a ratio ranging from 1:5 to 1:10.

12. A device for adding moisture to breathing gas of a patient, the device comprising:
- an evaporator defining an evaporator volume;
- a mixing chamber in communication with said evaporator volume, said mixing chamber also being in communication with the breathing gas of the patient, said mixing chamber being a separate structure from said evaporator;
- a first connection between said mixing chamber and said evaporator, said first connection being repetitively connectable of, and disconnectable from, said mixing chamber and said evaporator;
- a heater arranged outside of said evaporator and in a heat conducting connection with said evaporator, said heater being a separate structure from said evaporator;
- a second connection between said evaporator and said heater, said second connection being repetitively connectable and disconnectable of said evaporator and said heater;
- a liquid storage tank in communication with said evaporator, said liquid storage tank being larger than said evaporator;
- a flow channel connecting said liquid storage tank to said evaporator, said flow channel being formed of a material and having a size to thermally insulate said evaporator from said liquid storage tank.

13. A device in accordance with claim 12, further comprising:
- a breathing gas supply connected to said mixing chamber and supplying breathing gas to said mixing chamber and to the patient;
- a control circuit for controlling the supply of the breathing gas and for controlling said heater to add a predetermined amount of moisture to the breathing gas;
- said breathing gas supply, said heater and said control circuit being combined into a single appliance, said evaporator being repetitively connectable and disconnectable from said single appliance.

14. A device in accordance with claim 12, wherein: said first and second connections are repetitively connectable and disconnectable without significant destruction of a respective connection.

15. A device in accordance with claim 12, wherein: said evaporator is formed of a material having a higher heat conductivity than a material forming said liquid storage tank.

16. A device in accordance with claim 12, further comprising:
- a third connection in said flow channel, said third connection repetitively connecting and disconnecting said flow channel from said evaporator without significant destruction of said third connection.

17. A device in accordance with claim 12, further comprising:
- a pressure equalization line in communication with said evaporator and said liquid storage tank;
- said liquid storage tank being closed air tightly with a cover.

18. A device in accordance with claim 13, wherein:
- said first and second connections are repetitively connectable and disconnectable without significant destruction of a respective connection;
- said evaporator is formed of a material having a higher heat conductivity than a material forming said liquid storage tank;
- a third connection in said flow channel, said third connection repetitively connecting and disconnecting said flow channel from said evaporator without significant destruction of said third connection;
- a pressure equalization line in communication with said evaporator and said liquid storage tank;
- said liquid storage tank being closed air tightly with a cover.

19. A device in accordance with claim 16, wherein: said liquid storage tank, said flow channel and said evaporator being arranged in an arrangement for said liquid storage tank to fill said evaporator by a gravity flow from said liquid storage tank through said flow channel and into said evaporator, said arrangement maintaining an equal liquid level in both said liquid storage tank and said evaporator.

20. A device in accordance with claim 19, wherein:
a pressure equalization line is in communication with said evaporator and said liquid storage tank, said third connection also repetitively connecting and disconnecting said pressure equalization line from said evaporator without significant destruction of said third connection;
said liquid storage tank is closed air tightly with a cover;
a heated base or bottom surface of said evaporator is smaller than a base or bottom surface of said liquid storage tank by a ratio ranging from 1:5 to 1:10.

* * * * *